(12) United States Patent
Prineppi

(10) Patent No.: US 7,992,244 B2
(45) Date of Patent: Aug. 9, 2011

(54) ELECTRIC TOOTHBRUSHES

(76) Inventor: Frank J. Prineppi, Ft. Lauderdale, FL (US)

( * ) Notice: Subject to any disclaimer, the term of this patent is extended or adjusted under 35 U.S.C. 154(b) by 0 days.

(21) Appl. No.: 12/976,665

(22) Filed: Dec. 22, 2010

(65) Prior Publication Data

US 2011/0146010 A1 Jun. 23, 2011

Related U.S. Application Data

(60) Continuation of application No. 11/455,534, filed on Jun. 19, 2006, now abandoned, which is a continuation of application No. 11/006,818, filed on Dec. 8, 2004, now abandoned, which is a continuation of application No. 10/797,899, filed on Mar. 10, 2004, now abandoned, which is a division of application No. 09/969,632, filed on Oct. 4, 2001, now abandoned.

(51) Int. Cl.
*A61C 17/34* (2006.01)
(52) U.S. Cl. .................. 15/22.1; 15/28; 15/167.1
(58) Field of Classification Search .............. 15/22.1, 15/28, 167.1
See application file for complete search history.

(56) References Cited

U.S. PATENT DOCUMENTS

| | | | |
|---|---|---|---|
| 2,140,307 A | 12/1938 | Belaschk | |
| 4,353,660 A | 10/1982 | Parks | |
| 5,226,206 A | 7/1993 | Davidovitz et al. | |
| 5,353,460 A | 10/1994 | Bauman | |
| 5,617,603 A | 4/1997 | Mei | |
| 5,625,916 A | 5/1997 | McDougall | |
| 5,836,030 A | 11/1998 | Hazeu et al. | |
| 6,092,252 A | 7/2000 | Fischer et al. | |
| 6,138,310 A | 10/2000 | Porper et al. | |
| 6,178,579 B1 | 1/2001 | Blaustein | |
| 6,314,606 B1 | 11/2001 | Hohlbein | |
| 6,371,294 B1 | 4/2002 | Blaustein et al. | |
| 6,434,773 B1 | 8/2002 | Kuo | |
| 6,463,615 B1 | 10/2002 | Gruber et al. | |
| 2001/0054561 A1 | 12/2001 | Blaustein | |
| 2003/0205492 A1 | 11/2003 | Ferber | |

(Continued)

FOREIGN PATENT DOCUMENTS

EP 0537465 4/1993

(Continued)

OTHER PUBLICATIONS

International Search Report, Application No. PCT/US2005/002124, mailed Jul. 29, 2005.

(Continued)

*Primary Examiner* — Shay L Karls
(74) *Attorney, Agent, or Firm* — Judy W. Chung

(57) ABSTRACT

In a first embodiment an electric toothbrush having a housing containing an electric motor, the motor being drivingly connected to a first brush head rotatably mounted on an end of the toothbrush remote from the motor and adjacent to at least one other rotatable brush head. In a second embodiment a packaged electric toothbrush including a "try me" facility for remotely testing the operation of the toothbrush, which "try me" feature comprises a two-sided metal strip such as aluminum foil, separated by a dielectric material, respective sides of the strip being connected at one end to respective parts used to operate the electric toothbrush and the other end of the strip being folded over and including a centrally disposed aperture onto which is a bendable metal connector such that upon bending or pressing of the connector the two sides of the strip are electrically connected together to temporarily operate the toothbrush whilst still in its packaging.

20 Claims, 4 Drawing Sheets

U.S. PATENT DOCUMENTS

2003/0221267 A1    12/2003    Chan
2004/0143917 A1    7/2004    Ek

FOREIGN PATENT DOCUMENTS

| | | |
|---|---|---|
| EP | 1059049 | 12/2000 |
| GB | 2359739 | 9/2001 |
| RU | 2141278 | 11/1999 |
| RU | 2161018 | 12/2000 |
| WO | 02087464 | 11/2002 |
| WO | 03101338 | 12/2003 |

OTHER PUBLICATIONS

Office Aciton from the European Patent Office dated Aug. 12, 2006 for corresponding European Patent Application No. EP 05 751 117.2.

Decision on Grant from the Patent Office of Russia dated Aug. 14, 2006 for corresponding Russian Patent Application No. 2004113437/14(014555).

Office Action from the Patent Office of Russia dated Nov. 6, 2008 for corresponding Russian Patent Application No. 2006130372.

Office Action from the Patent Office of China dated Jun. 5, 2009 for corresponding Chinese Patent Application No. 200580008650.X.

Office Action from the European Patent Office dated Dec. 17, 2009 for corresponding European Patent Application No. EP 02 767 679.0.

ELECTRIC TOOTHBRUSHES

CROSS-REFERENCE TO RELATED APPLICATIONS

This application is a continuation of application Ser. No. 11/455,534, filed Jun. 19, 2006, which is a continuation of application Ser. No. 11/006,818, filed Dec. 8, 2004, which is a continuation of application Ser. No. 10/797,899, filed Mar. 10, 2004, which claims the benefit of application Ser. No. 09/969,632, filed Oct. 4, 2001, all of which are incorporated herein in their entirety.

FIELD OF THE INVENTION

This invention relates to electric toothbrushes including those powered by a rechargeable battery from a mains domestic electricity supply.

BACKGROUND OF THE INVENTION

In U.S. Pat. No. 5,226,206, there is described an electric toothbrush having twin brush heads which are drivingly connected together by a rack and pinion assembly in which the rack is reciprocated via a drive shaft connected to a crank shaft mounted at one end for rotation on a gear driven by a motor. The twin brush heads are therefore able to oscillate about their respective axes either in the same direction or in opposite directions, depending upon the configuration of the rack, this being generally 'U' shaped so as to facilitate the use of gear teeth on the inside thereof for driving the respective heads via respective pinions in mesh therewith.

A potential problem with this arrangement is that it is relatively complex and is not easily cleanable with running water such that the moving parts may become clogged with toothpaste or debris. In addition, the complexity and number of the parts used to provide the oscillating motion for the twin heads adds to the cost and complexity of manufacture.

In U.S. Pat. No. 5,353,460 the use of a rack and pinion assembly is dispensed with in favour of a crank mechanism connecting the first brush head to the second brush head. The first brush head is directly driven by a miter gear or crown wheel which then, in turn, drives the second brush head to oscillate in the opposite direction to that of the first brush head. This arrangement involves fewer moving parts but still depends on the presence of gears and the crank mechanism for its operation, leading to the possibility of these moving parts being difficult to clean and becoming clogged etc. In addition, because the crank arm necessarily has to connect the respective brush heads on the sides thereof remote from the bristles, it will be understood that additional space is required to provide for free movement of the crank arm when the brush is in use. This also has the disadvantage in that the working ends of the crank linkage can never be directly exposed to running water for rinsing and cleaning purposes.

In a first aspect the present invention is derived from the realization that it would be preferable to have an electric toothbrush having multiple, such as two, rotatable brush heads but which dispenses with the need for gears or crank mechanisms for transferring oscillating rotary motion from one brush to another, typically a first brush driven by a connection to an electric motor and the second brush driven by movement of the first brush.

BRIEF SUMMARY OF THE INVENTION

According to a first aspect of the invention there is provided an electric toothbrush having a housing containing an electric motor, the motor being drivingly connected to a first brush head rotatably mounted on an end of the toothbrush remote from the motor adjacent to at least one other rotatable brush head, wherein the first brush head includes a drive pin extending therefrom substantially at right angles from the axis of rotation, the free end of the drive pin being received within a guide slot in a brush head to be driven thereby, the arrangement being such that the drive pin bears against respectively opposite sides of the guide slot to thereby drive a driven brush head clockwise and anti-clockwise about its axis of rotation as the first brush head is also being oscillated.

This arrangement has the advantage in that the connection between two or more brush heads is extremely simple and since there are no moving parts other than the free end of the or each drive pin as it rocks back and forth within the or a respective guide slot, such can be easily cleaned under running water. A further advantage is that the mechanical motion of the brush head driven by the first brush head is necessarily magnified slightly due to its displacement from the first brush head and this overcomes any backlash that may be inherent in the system. Although a preferred embodiment of the invention uses only two brush heads, one driven directly via the drive link between the electric motor and the brush itself and the other being driven by a drive pin extending from the periphery of the first brush head, nevertheless it will be apparent that the same principle can be used to drive more than a second brush head and, in turn, the second brush head may itself drive a third brush head, and so on. Additionally, one or more of the brush heads may be of different diameter to the first brush head, although it will be appreciated that where there are differences in diameter a consideration of equivalent gear ratios then becomes necessary to determine whether the difference is too great to allow for the required movement.

The means by which the first brush head is driven back and forth about its axis may comprise a bell crank arrangement in which an elbowed end of a crankshaft, drivingly connected at its other end to the motor, is received within an elongated slot extending into the periphery of the first brush head diametrically opposite the drive pin (for a twin brush head toothbrush), the length of the slot being at least as great as the range of movement available to the elbow when the crankshaft is rotated through 360.degree.

The use of a drive pin for driving a second brush head has a still further advantage to the linkages referred to in the preamble hereto in that the second head may have a plane of rotation which is angled relative to the plane of rotation of the first brush head, such as being angled inwardly slightly, although it will be understood that there are practical limits to the amount that a second or even more such brush heads can be angled with respect to the plane of rotation of the first brush head.

Preferably, the end of the elbowed end of the crankshaft and the or each drive pin is partly spherical and takes the form of a ball joint, each being receivable within a respective slot of substantially the same diameter so as to minimize rattle and wear. A convenient arrangement has been found to be a ball joint made of nylon where the bristle holding part of the brush heads are made of e.g. PVC or some other suitable plastics material. Preferably, the slot for receiving each ball joint is partly arcuate so as to maximize the surface area in contact between the ball joint to thereby decrease the load forces on the slot and therefore reduce wear.

According to a second embodiment of the invention, the toothbrush is packaged in e.g. a blister pack and includes a "try me" facility for remotely testing the operation of the toothbrush, such as by a prospective purchaser of the toothbrush, whilst the toothbrush is still in its protective sales packaging, which "try me" feature comprises a two-sided metal foil or strip (such as aluminum foil), separated by a di-electric material such as paper or plastics, respective sides of the foil or strip being connected at one end to respective conductors of an electric circuit used to operate the electric toothbrush and, in particular, to energize the electric motor thereof, the other end of the foil or strip being folded over and including a centrally disposed aperture onto or over which is disposed a bendable metal connector such that upon bending or pressing of the connector the two sides of the strip or foil are electrically connected together to temporarily operate the toothbrush whilst still in its packaging.

Preferably, the "try me" feature may be permanently disconnected from the toothbrush after being purchased by simply being pulled away from the electrical connectors to which it is attached.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The invention will now be described, by way of example only, with reference to the accompanying drawings in which.

DETAILED DESCRIPTION OF THE INVENTION

The following description of the preferred embodiment(s) is merely exemplary in nature and is in no way intended to limit the invention, its application, or uses.

Figure 1:
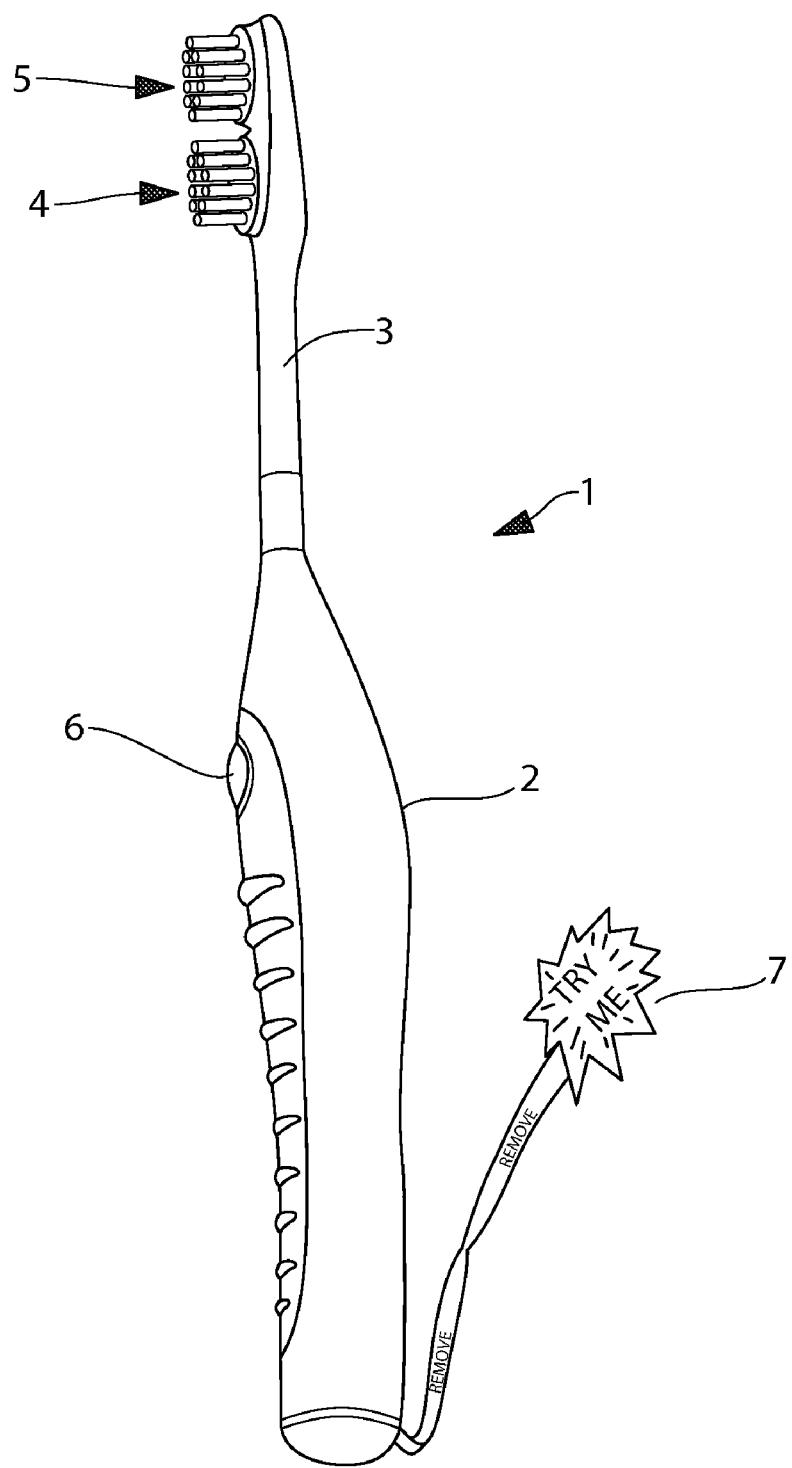
FIG. 1 is a side elevation of a toothbrush according to a first embodiment of the invention having a pair of brush heads, one of which is angled inwardly slightly with respect to the other.

Referring firstly to FIG. 1, an electric toothbrush shown generally at 1 comprises a plastics body portion 2 for housing a motor, battery and associated electrical circuitry (not shown) and a detachable generally hollow brush head holder 3 including at the free end thereof a first brush head 4 and a second brush head 5, each being partly rotatable by being drivingly connected to the motor in the housing 2 in a manner to be described. A push button 6 in the housing 2 is used to operate the toothbrush 1 and a "try me" feature shown generally at 7 can be used to temporarily operate the toothbrush 1 in accordance with a second embodiment of the invention in a manner to be described with reference to FIG. 6.

Figure 2:
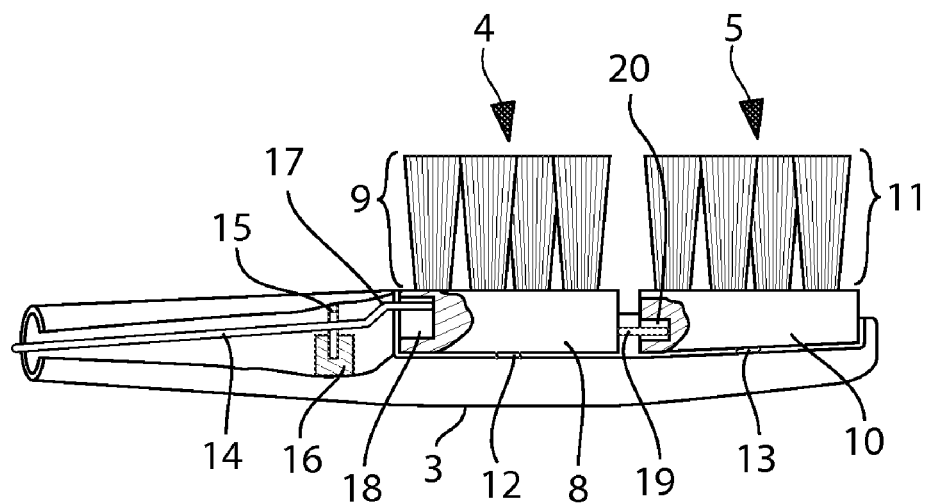
FIG. 2 is an enlarged and partly cut away view of the end of the toothbrush of FIG. 1 which includes the brush heads.
Figure 3:
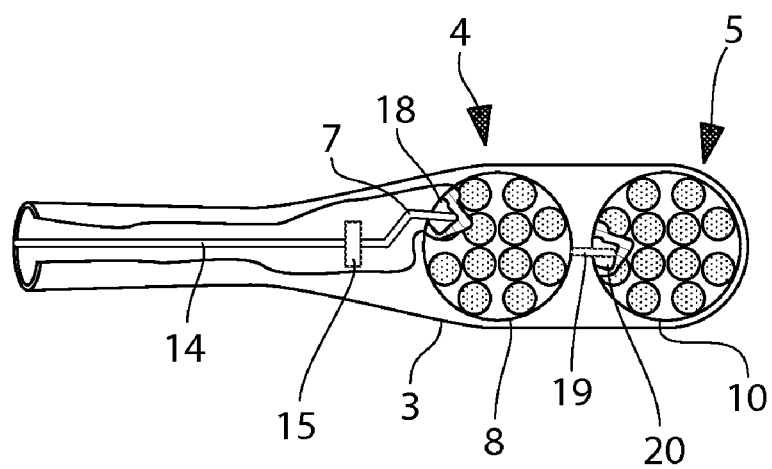
FIG. 3 is a schematic plan view showing the mode of operation of the toothbrush heads of FIGS. 1 and 2.

In FIGS. 2 and 3 there is shown the operable end of the brush head holder 3 in which it will be seen that the first brush head 4 includes a generally disc-shaped bristle holder 8 from which extend respective sets of bristles shown generally at 9 in FIG. 2. similarly, the second brush head 5 comprises a generally disc-shaped bristle holder 10 from which extend sets of bristles shown generally at 11. Brush head 4 is mounted for rotation on a pivot pin 12 and brush head 5 is mounted for rotation on a pivot pin 13, although the plane of rotation of brush head 5 is slightly offset to the plane of rotation of brush head 4 by about 5.degree. such that the bristles 11 are inclined slightly inwardly towards the bristles 9. This has been found to be advantageous in that the brush heads 4,5 can collectively clean a greater surface area of teeth than would be the case if both were rotatable in the same plane, by virtue of the generally curved placement of teeth within a mouth.

Reciprocating clockwise and anti-clockwise rotation of the first brush head 4 is facilitated by means of a bell crank mechanism which includes a stainless steel crankshaft 14 secured for rotation about its major axis in a journal 15 extending from a spigot 16 on the inside of the brush head holder 3 as shown more clearly in FIG. 2. The end of the crankshaft adjacent thereto includes an elbow joint 17, the free end of which extends into a slotted region 18 within the bristle holder 8 of the brush head 4, which slotted region 18 is sufficiently long (or tall) to accommodate 360.degree. rotation of the crankshaft 14 and in particular movement of the elbow 17 about the major axis of the crankshaft 14 so that upon rotation thereof continuously clockwise or anti-clockwise it will be apparent that the brush head 4 will be forced to oscillate back and forth about the pivot 12.

Brush head 5 is driven in a different manner by means of a drive pin 19 which extends diametrically outwardly from the bristle holder 8 of the brush 4, to which it is fixed for rotation therewith, and is received in a slotted region 20 of the bristle holder 10 of the brush head 5. In this case, the slotted region 20 is wide enough to permit the drive pin 19 to move in an arc dictated by the movement of the elbow 17 within the slotted region 18 about the major axis of the crankshaft 14 but in an opposite sense so that clockwise movement of the brush head 4 causes anticlockwise movement of the brush head 5, and vice versa.

As will be understood by those skilled in the art, the absence of any gears in this part of the electric toothbrush 1 enables it to be easily cleaned in running water and because there are few moving parts as compared to toothbrushes which include gears or crank arms for driving the or each brush head it will be appreciated that manufacture of the toothbrush according to the first embodiment of the invention can be easily facilitated.

Figure 5:
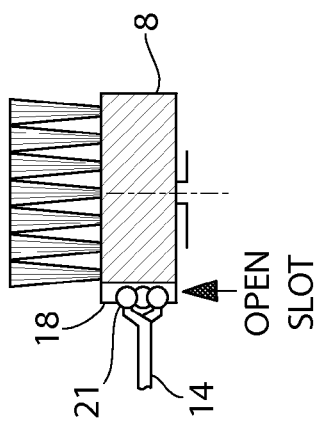
Figure 4:
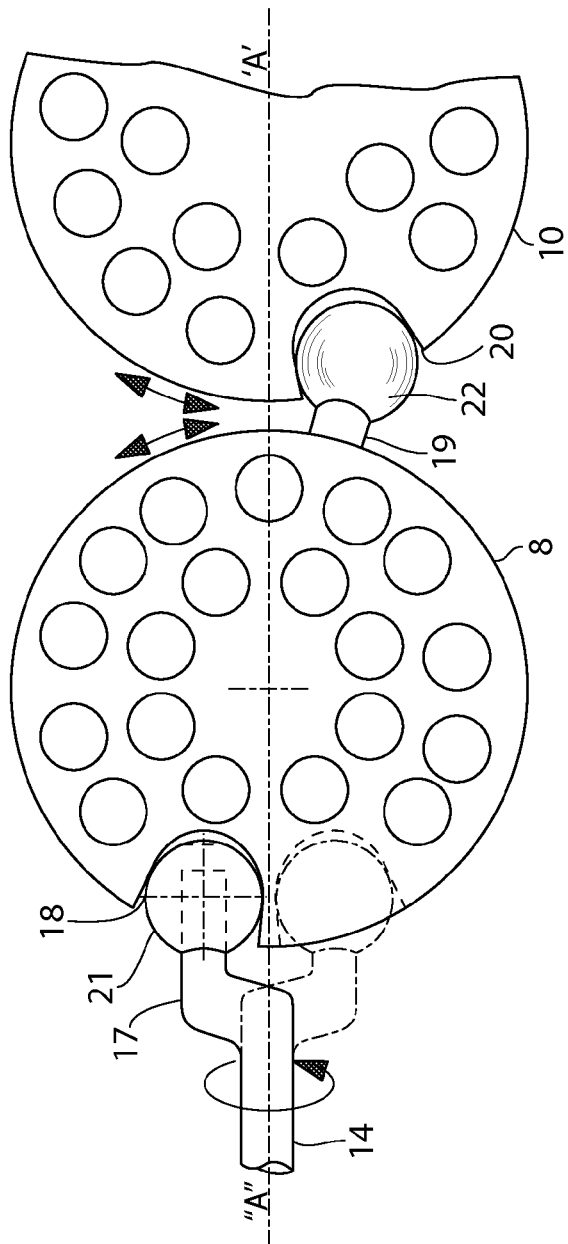
FIG. 4 is an enlarged schematic view of the brush head end of a toothbrush according to a preferred embodiment of the invention, and, FIG. 5 is a section of elevation along the line "A"-"A" of part of FIG. 5.

In FIGS. 4 and 5 there is shown a preferred embodiment of the engagement between the elbowed end 17 of the crankshaft 14 with the slot 18 in the first brush head 8 and between the drive pin 19 within the slot 20 in the second brush head 10. In each case a respective part-spherical ball joint 21, 22 made of nylon are received within the respective slots 18, 20, which in this instance are partly arcuate so as to maximize the surface area available for contact by the ball joints 21, 22. This has the advantage of minimizing wear and in practice it has been found that the use of nylon in the ball joints 21, 22 gives excellent results in terms of self-lubrication properties when the brush heads 8,10 are made of a suitable plastics material, such as PVC. As well, it will be apparent that during use of the toothbrush, saliva and indeed debris from foodstuffs being cleaned will also assist in lubricating the moving parts, whereafter they may be cleaned in running water with little risk of particles of debris adhering to the generally smoothly profiled surfaces in this region of the toothbrush.

In FIGS. 4 and 5 the locus of movement of the ball joint 21 is shown in which it will be seen that as the crankshaft 14 rotates in one direction only the ball joint 21 essentially assumes maximum upper and lower positions about the central axis of the crankshaft 14 within the slot 18 as shown in FIG. 5 and left to right positions as shown in FIG. 4 to thereby drive the bristle holder 8 back and forth about its central axis in the manner shown arrowed to, in turn, drive the second bristle holder 10 via the drive shaft 14 back and forth about its own axis, but in the opposite sense so that as one brush head moves clock wise, the other always moves anti-clockwise, and so on.

Figure 6:
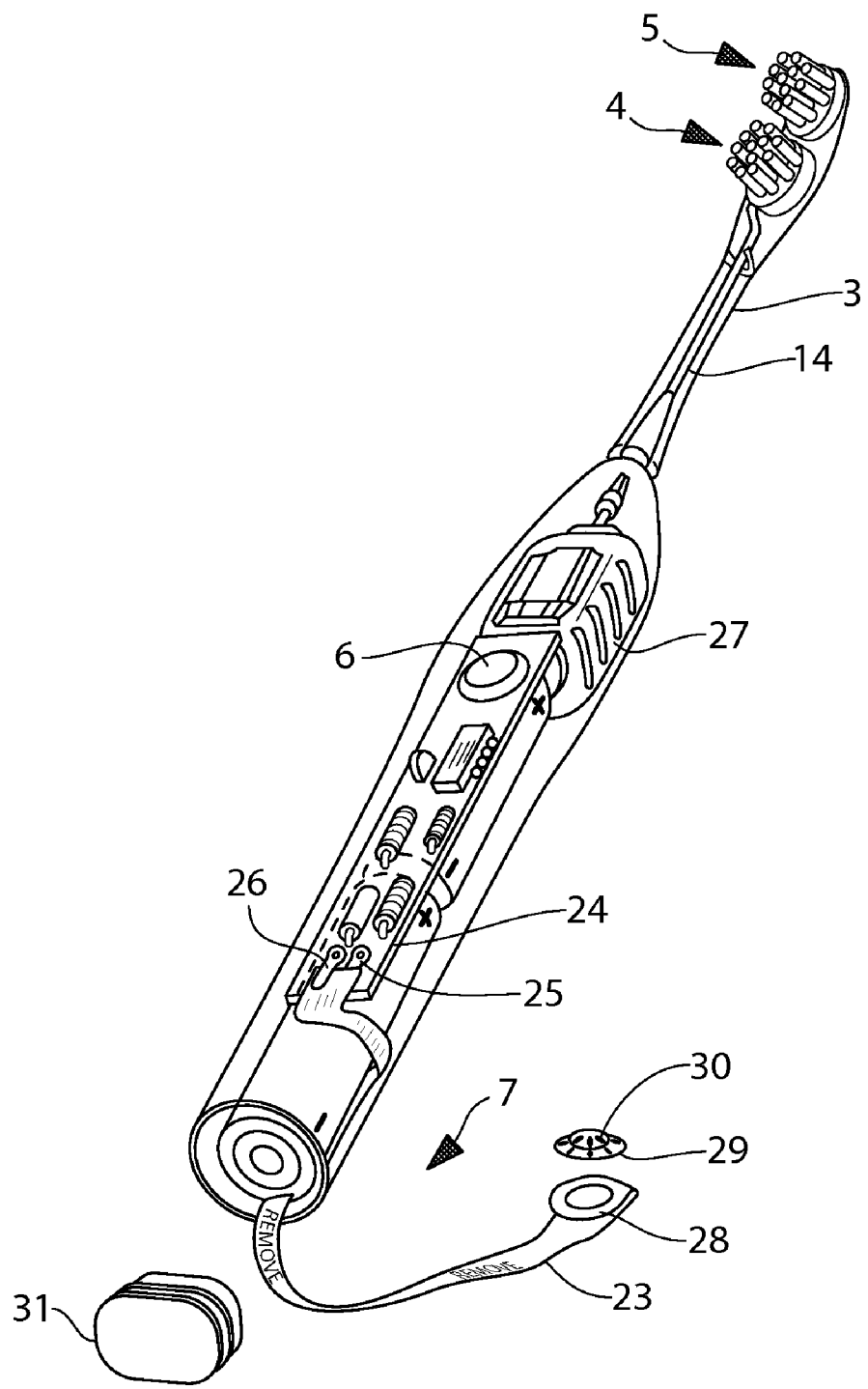
FIG. 6 is a perspective and partly cut away view of a second embodiment of the invention, which includes a "try me" feature.

In FIG. 6 there is shown a second embodiment of the invention which includes a "try me" feature shown generally at 7. This includes a twin sided metal foil strip 3, such as a double sided aluminum strip separated by a dielectric material (not shown) such as paper or plastics, respective sides of the strip 3 being electrically connected to respective parts of a printed circuit board 24 by connectors 25 and 26 forming part of a closeable circuit for operating a motor 27 to, in turn, rotate the crankshaft 14 and hence oscillate the brush heads 4, 5 in the manner as described with reference to FIGS. 2 and 3.

The free end of the strip 23 has a folded over region in the form of a ring 28 onto which can be fitted a metal disc 29 which includes a domed central region 30 which may be pressed to temporarily connect both sides of the strip 3 to complete the circuit between the connectors 25 and 26 and thereby temporarily activate the toothbrush 1. As will be appreciated, because the "try me" feature 7 includes a strip 23 by which it allows a prospective purchaser of the toothbrush to determine if and how it works prior to purchase following pressing of the metal disc 29, after purchase the "try me" feature 7 can be effectively deactivated by simply pulling the strip 23 away from the printed circuit board 24 and hence out of engagement with the connectors 25, 26 thereon, whereafter an end cap 31 can be refitted onto the housing 2 of the toothbrush 1 in order to commence normal operation via pressing of the button 6.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

What is claimed is:

1. An electric toothbrush comprising:
    an electric motor;
    a first brush head that is disc-shaped comprising
        a first pivot pin extending substantially perpendicular to a face of the first brush head, the first pivot pin having a first longitudinal axis extending substantially perpendicular to the face of the first brush head, the first brush head mounted for rotational movement about the first longitudinal axis;
    a second brush head having
        a second pivot pin extending substantially perpendicular to a face of the second brush head, the second pivot pin having a second longitudinal axis extending substantially perpendicular to the face of the second brush head, the second brush head mounted for rotational movement about the second longitudinal axis;
    a rotatable driving structure operatively connecting said motor to the first brush head and comprising a crankshaft defining a central axis of rotation, the crankshaft having a free end including a straight portion oriented parallel to and offset from the central axis of the crankshaft and an elbow connecting the straight portion to the crankshaft, the straight portion terminated with a spherical ball engaging a first guide slot defined in the first brush head, wherein rotation of the crankshaft through 360 degrees imparts oscillating motion to the first brush head about its first longitudinal axis; and
    a drive pin having a first end and a second end, the drive pin extending between said first brush head and said second brush head, wherein the first end of the drive pin is connected to one of said first brush head and said second brush head, and the second end of the drive pin is pivotably received in a second guide slot within one of the other of said first brush head and said second brush head,
    wherein said drive pin is independent of the driving structure and connected to said first brush head at a location displaced from the connection of the driving structure to said first brush head,
    wherein a ball joint is defined between each of the free end of the crankshaft of the driving structure and the first brush head, and the first brush head and the second brush head, said second guide slot having an arcuate surface for receiving the ball joint, wherein said first brush head rotates about said first longitudinal axis of said first pivot pin and said second brush head rotates about said second longitudinal axis of said second pivot pin.

2. An electric toothbrush according to claim 1, further comprising a housing containing said motor and wherein said first and second brush heads are mounted to the housing for oscillation about their respective first and second pivot pins.

3. An electric toothbrush according to claim 2 wherein said motor drives said first brush head in an oscillating manner, wherein as said first brush head oscillates the drive pin extending therefrom bears against the respective sides of said second guide slot to thereby drive said second head in an oscillating manner.

4. An electric toothbrush according to claim 1 wherein said second end is a ball and said second guide slot is formed to closely receive it therein.

5. An electric toothbrush according to claim 1 wherein said first brush head is located between said electric motor and said second brush head.

6. An electric toothbrush comprising:
    a body portion;
    a brush head holder portion having a free end projecting from the body portion;
    an electric motor secured within the body portion;
    a first brush head having
        a first pivot pin extending substantially perpendicular to a face of the first brush head, the first pivot pin forming a first longitudinal axis extending substantially perpendicular to the face of the first brush head, the first brush head portion mounted by means of the first pivot pin to the brush head holder portion for rotational movement about the first longitudinal axis,
    a second brush head having
        a second pivot pin extending substantially perpendicular to a face of the second brush head, the second pivot pin having a second longitudinal axis extending substantially perpendicular to the face of the second brush head, the second brush head portion mounted by means of the second pivot pin to the brush head holder portion for rotational movement about the second longitudinal axis,
    a drive shaft operatively connected to and driven by said electric motor, said drive shaft operatively connected to said first brush head for driving the rotational movement of said first brush head, the drive shaft defining a central axis of rotation and having a free end including a straight portion oriented parallel to and offset from the central axis of the drive shaft and an elbow connecting the straight portion to the drive shaft, the straight portion terminated with a spherical ball engaging a first guide slot defined in the second brush head, wherein rotation of the crankshaft through 360 degrees imparts oscillating motion to the second brush head about its second longitudinal axis; and a drive pin independent of the drive shaft having a first end, said first end mounted to said first brush head at a location displaced from the connection of said drive shaft to said first brush head and having a longitudinal axis that extends diametrically from the first brush head toward the second brush head, said second end of said drive pin extending into a second guide slot with the second brush head whereby said drive pin connects said first and said second brush heads without the need for other supporting structure, said drive pin being located at said first brush head at a location displaced from the location of the drive connection of said drive shaft to said first brush head, and wherein movement imparted to said first brush head by said drive shaft is transmitted to said second brush head through said drive pin by said first drive head for simultaneous movement of both said first brush head and said second brush head.

7. An electric toothbrush according to claim 6 wherein said electric motor is mounted in a hollow housing defined by the body portion, and said drive shaft through said brush head portion.

8. An electric toothbrush according to claim 7 wherein each of said first brush head and said second brush head is mounted on a pivot structure within said brush head portion for rotational movement about their respective first and second rotational axes.

9. An electric toothbrush according to claim 8 wherein each of said brush heads is of disc shape, and further comprising bristles extending outwardly from the face of each said brush heads.

10. An electric toothbrush according to claim 6 wherein said first end of said drive pin is fixed to said first brush head.

11. An electric toothbrush according to claim 10 wherein said drive pin is mounted to said first brush head in a cantilevered manner.

12. An electric toothbrush according to claim 10 wherein said first brush head is located between said second brush head and said motor.

13. An electric toothbrush according to claim 6 wherein each of said brush heads is movably mounted for rotational oscillation in clockwise and counterclockwise directions.

14. An electric toothbrush according to claim 6 wherein said second end of said drive pin terminates in a ball closely received in said second guide slot within said second brush head.

15. An electric toothbrush according to claim 6 further comprising a third brush head, a third guide slot in said third brush head and a further drive pin mounted to one of said first brush head and said second brush head at one end thereof with a second end being mounted in said third guide slot of said third brush head.

16. An electric toothbrush according to claim 6 wherein each of said brush heads is movably mounted in a rotational manner, and said drive pin being perpendicular to the axis of rotation of said first brush head.

17. An electric toothbrush according to claim 6 wherein each of said brush heads is movable in a rotational manner, each of said brush heads having an outer surface rotatable in a plane, and said plane of said second brush head being at an angle to said plane of said first brush head.

18. An electric toothbrush according to claim 17 wherein said plane of said second brush head is inclined inwardly toward said plane of said first brush head.

19. An electric toothbrush according to claim 6 wherein said brush head holder portion is detachably mounted to said body portion.

20. An electric toothbrush comprising:
a housing containing an electric motor;
a detachable brush head holder coupled to a body portion for housing the motor;
a first disc-shaped brush head rotationally mounted to the holder about a first pivot pin extending substantially perpendicular to a face of the first brush head, the first pivot pin defining a first axis extending substantially perpendicular to the face of the first brush head;
a crankshaft extending longitudinally from the motor and drivingly connecting the motor to the first brush head, the crankshaft defining a longitudinal axis of rotation and being rotatable a full 360 degrees by the motor, the crankshaft mounted to the motor in a manner that prevents longitudinal movement with respect to the housing when the crankshaft is rotated by the motor, the crankshaft having a free end including a straight portion oriented parallel to and offset from the longitudinal axis of the crankshaft and an elbow connecting the straight portion to the crankshaft, the straight portion terminated with a spherical ball engaging a vertically-extending first slot defined in a peripheral sidewall of the first brush head, wherein rotation of the crankshaft through 360 degrees moves the ball up and down in the slot to impart oscillating rotational clockwise and counterclockwise motions to the first brush head about the first axis;
a second disc-shaped brush head rotationally mounted to the holder about a second pivot pin extending substantially perpendicular to a face of the second brush head, the second pivot pin defining a second axis extending substantially perpendicular to the face of the second brush head;
a drive pin independent of the crankshaft and having a first end engaging a portion of the first brush head sidewall that is displaced from and diametrically opposed to the first slot in the sidewall engaged by the crankshaft, the drive pin further having a second end engaging a second slot defined in a peripheral sidewall of the second brush head, the first and second slots of the first and second brush heads respectively being in approximate alignment with the longitudinal axis of the crankshaft,
wherein clockwise rotation of the first brush head by the crankshaft causes the second brush head to rotate in an opposite counterclockwise direction and counterclockwise rotation of the first brush head causes the second brush head to rotate in an opposite clockwise direction.

* * * * *